United States Patent [19]
Walker et al.

[11] Patent Number: 5,288,964
[45] Date of Patent: Feb. 22, 1994

[54] ELECTRICAL APPARATUS FOR DESTROYING A MEDICAL INSTRUMENT

[76] Inventors: Robert M. Walker, 10093 Camp Rd., West Salem, Ohio 44287; Roger A. Kimmel, Jr., 761 Parkview Dr., Aurora, Ohio 44202

[21] Appl. No.: 986,740
[22] Filed: Dec. 8, 1992
[51] Int. Cl.⁵ .................................. F23K 11/22
[52] U.S. Cl. .................................................. 219/68
[58] Field of Search ............................ 219/68, 69.1

[56] References Cited

U.S. PATENT DOCUMENTS

| | | | |
|---|---|---|---|
| 4,628,169 | 12/1986 | Ch'ing-Lung | 219/68 |
| 4,877,934 | 10/1989 | Spinello | 219/68 |
| 4,961,541 | 10/1990 | Hashimoto | 219/68 |
| 4,965,426 | 10/1990 | Colombo | 219/68 |
| 5,076,178 | 12/1991 | Kohl et al. | 219/68 |
| 5,077,456 | 12/1991 | St. Louis | 219/69.1 |
| 5,091,621 | 2/1992 | Butler | 219/68 |
| 5,138,124 | 8/1992 | Kirk et al. | 219/68 |
| 5,138,125 | 8/1992 | Salesses | 219/68 |
| 5,212,362 | 5/1993 | Burden et al. | 219/69.1 |

*Primary Examiner*—Geoffrey S. Evans

[57] ABSTRACT

An apparatus for destroying a medical instrument includes a housing having a wall member with an aperture disposed therein. A first electrical connector member is mounted adjacent the wall member of the housing for engaging a portion of a medical instrument inserted through the aperture in the wall member. A second electrical connector member is disposed within the housing for engaging an end portion of a medical instrument inserted through the aperture in the wall member. The first and second electrical connector members are provided to be selectively connected to a supply of electric current for destroying the medical instrument by transmitting current from the first electrical connector member to the second electrical connector member and through a medical instrument for melting the same. The second electrical connector member may be spring biased toward the aperture and pivotally mounted.

7 Claims, 5 Drawing Sheets

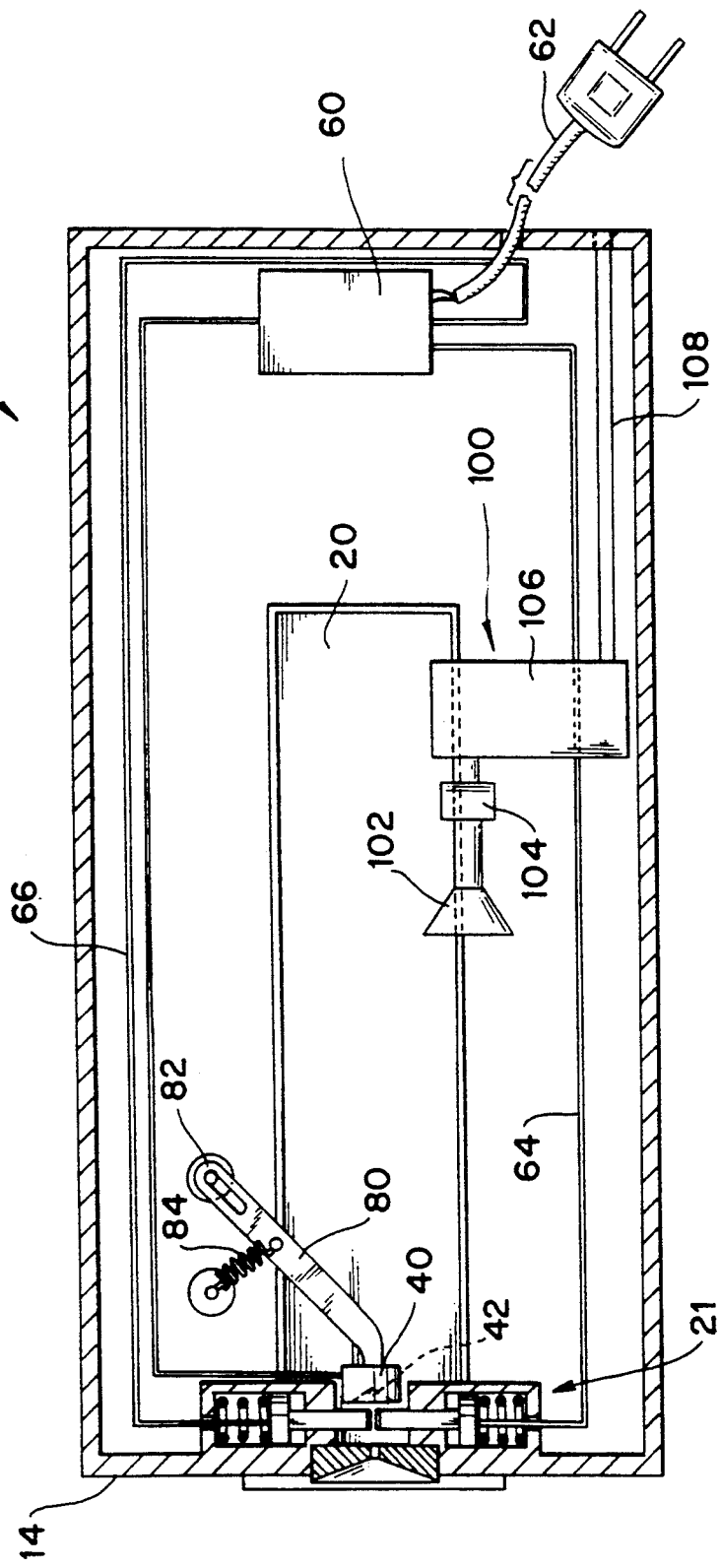

ELECTRICAL APPARATUS FOR DESTROYING A MEDICAL INSTRUMENT

BACKGROUND OF THE INVENTION

1. Field of the Invention

The present invention is directed to an apparatus for destroying a medical instrument by means of transmitting electrical current through the instrument to melt the same.

2. Description of Background Art

Hithertofore, medical instruments, for example, needles, syringes, scalpels, sutures, etc., require disposal by means of inserting the medical instrument into an authorized container which is puncture-proof. Such a container is designed to ensure that the disposal of the medical instrument will not cause any accidental puncturing of an individual involved with the handling of the medical instrument.

Unfortunately, the disposal of medical instruments is a very serious task which requires a great deal of attention to detail to ensure that an individual does not accidentally prick himself/herself during the disposal of the medical instrument. No prior art device is known to the present inventors which enables an individual to actually destroy the medical instrument by means of transmitting electric current therethrough in order to melt the same.

SUMMARY AND OBJECTS OF THE PRESENT INVENTION

It is an object of the present invention to provide an apparatus for destroying a medical instrument wherein the medical instrument is actually melted by means of transmitting an electric current therethrough.

Another object of the present invention is to provide an apparatus for destroying a medical instrument which includes at least one electrode disposed within a housing which is mounted for movement therein in order to accommodate medical instruments of variable sizes.

These and other objects of the present invention are provided by an apparatus for destroying a medical instrument wherein at least one carbon brush is mounted adjacent to an aperture in a housing for engaging a portion of the medical apparatus and a second electrical connector is disposed within the housing for engaging an end portion of the medical instrument. The first and second electrical connectors are adapted to be selectively connected to a supply of electric current for destroying the medical instrument by transmitting current from the first electrical connector means to the second electrical connector means and through a medical instrument for melting the same.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 5 is a side view of another embodiment of the present invention wherein the second electrode is pivotally mounted within the housing.

DETAILED DESCRIPTION OF THE PREFERRED EMBODIMENTS

Figure 1:
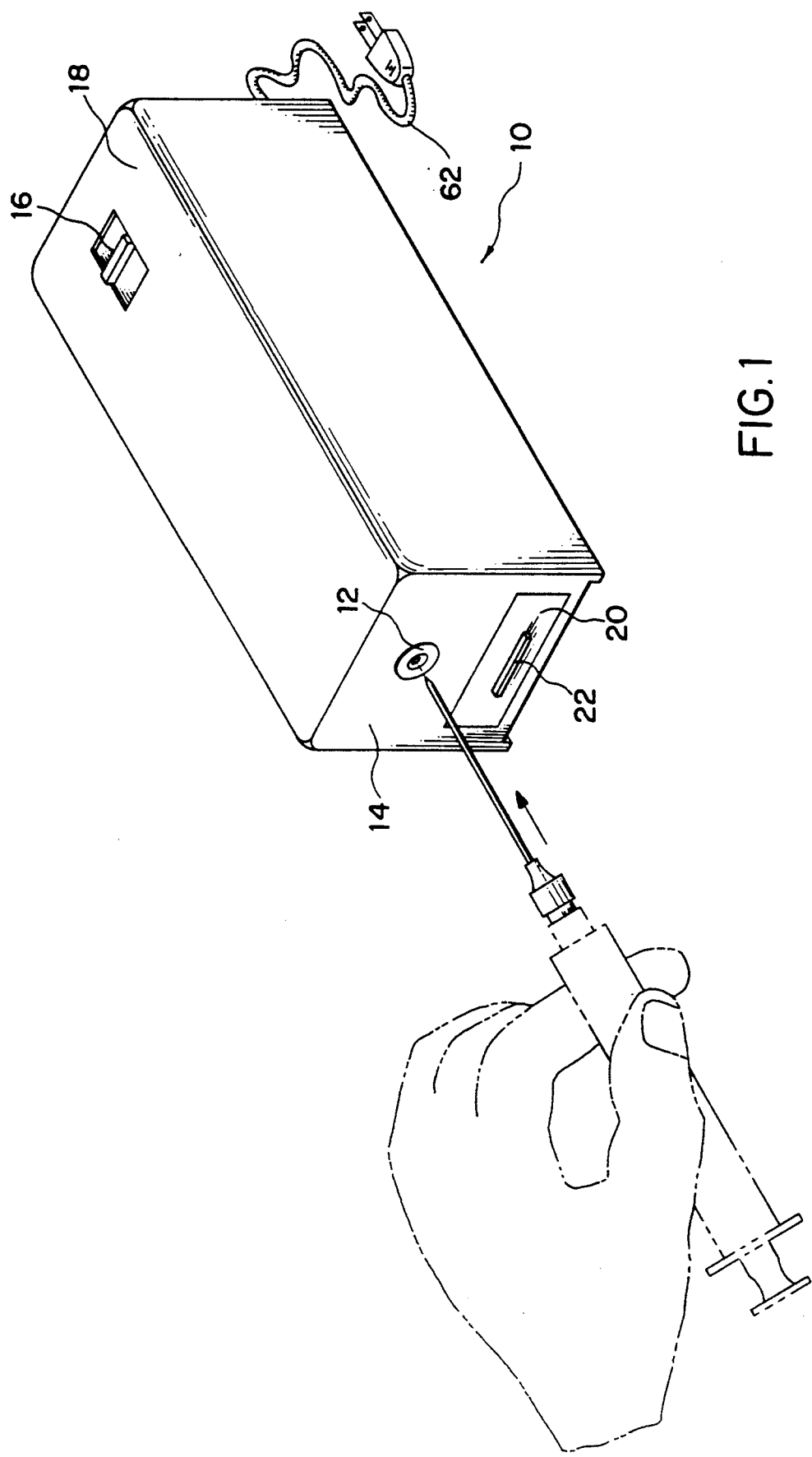
FIG. 1 is a perspective view illustrating an apparatus for destroying a medical instrument according to the present invention.

As illustrated in FIG. 1, a housing 10 is provided with an aperture 12 disposed within a wall member 14. An actuating switch 16 is positioned on the wall member 18. The switch member 16 may be disposed at any location on the outer surface of the housing 10. A drawer 20 is provided with a handle 22. The drawer 20 is operatively disposed to slide within the housing 10. The drawer 20 receives molten metal from medical instruments destroyed within the apparatus during use.

Figure 2:
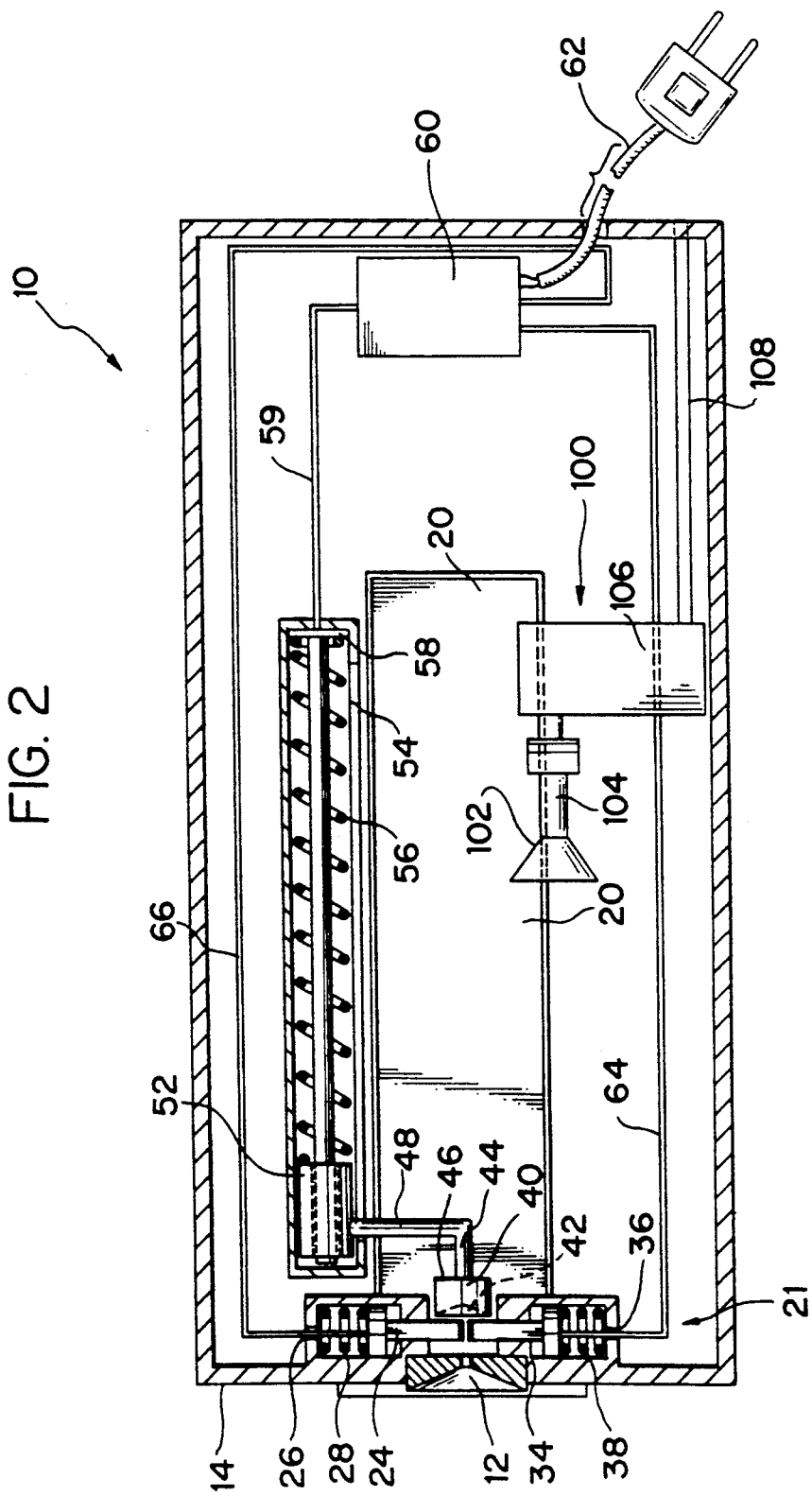
FIG. 2 is a top plan view partially cut away to show the operating features of the present invention.

FIG. 2 illustrates a partial cut-away view of the operating features of the present invention. A carbon brush 24 is operatively disposed within a housing 26. Biasing means, for example, a spring 28 is provided within the housing 26 to bias the carbon brush 24 to project outwardly from the housing 26. Similarly, a brush 34 is disposed within a housing 36. Biasing means, for example, a spring 38, is mounted within the housing 36 to bias the carbon brush 34 outwardly from the housing 36. The carbon brushes 24, 34 are concentrically aligned with the aperture 12. In this way, when a medical instrument, for example, a needle or scalpel is disposed within the aperture 12, the needle or scalpel will be engaged by the brushes 24, 34. A second electrical connector means 40 is mounted adjacent to and in alignment with the aperture 12. In this way, as a needle 50 or a scalpel projects through the aperture 12 and is engaged at a portion by means of the carbon brushes 24, 34, the tip of the needle 50 or scalpel will engage the second electric connector means 40. The second electrical connector means 40 includes a conical surface 42 for centering the needle or scalpel as it is positioned within the housing 10. The support 44 is connected to an end 46 of the second electrical connector means 40. A mounting arm 48 is affixed to one end of the support 44.

The mounting arm 48 is mounted on an electrically conductive support 52 which is disposed within an electrically insulated tubular member 54. The electrically conductive support 52 is engaged with a spring 56 for biasing the electrically conductive support 52 in the direction of the wall 14. The spring 56 may be constructed of phosphor bronze or other electrically conductive material so as to permit electric current to be conveyed therealong. An electrical connector 58 is mounted to the spring 56. An electric supply line 59 is operatively connected to the support 58 and to a transformer 60. The transformer 60 receives electrical power from the supply line 62 and transforms the AC electrical supply into DC current. An electrical line 64 is operatively connected to the transformer 60 and the carbon brush 34. Similarly, an electrical line 66 is operatively connected to the transformer 60 and the carbon brush 24.

Figure 3:
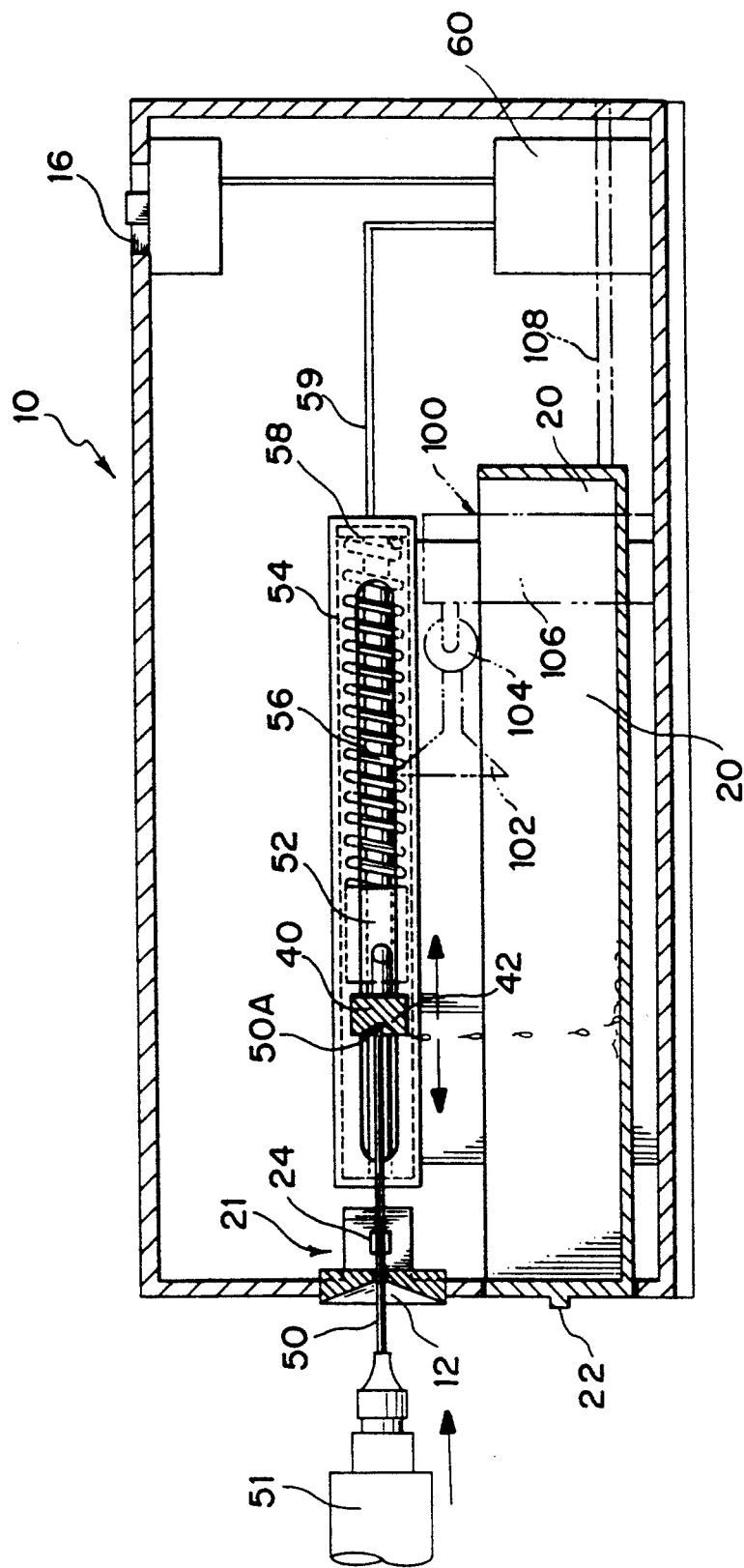
FIG. 3 illustrates a side view of the present invention wherein a needle attached to a syringe is being melted.

As illustrated in FIG. 3, similar elements as set forth in FIG. 2 include the same reference numerals.

A needle 50 connected to a syringe 51 is inserted through the aperture 12. The needle 50 includes a sharpened point 50A at its outer end. The sharpened point 50A engages the conical recess 42 disposed within the second electrical connector means 40. The carbon brushes 24, 34 engage a portion of the needle 50 as the needle 50 is inserted within the aperture 12. The sharpened end 50A engaged within the conical recess 42 of the second electrical connector means 40 permits the actuation of the electric current through the needle 50 to be accelerated so as to start the melting of the needle 50. Particles from the melted needle 50 will fall into the drawer 20 disposed beneath the first electrode means 21 and the second electrical connector means 40.

Figure 4:
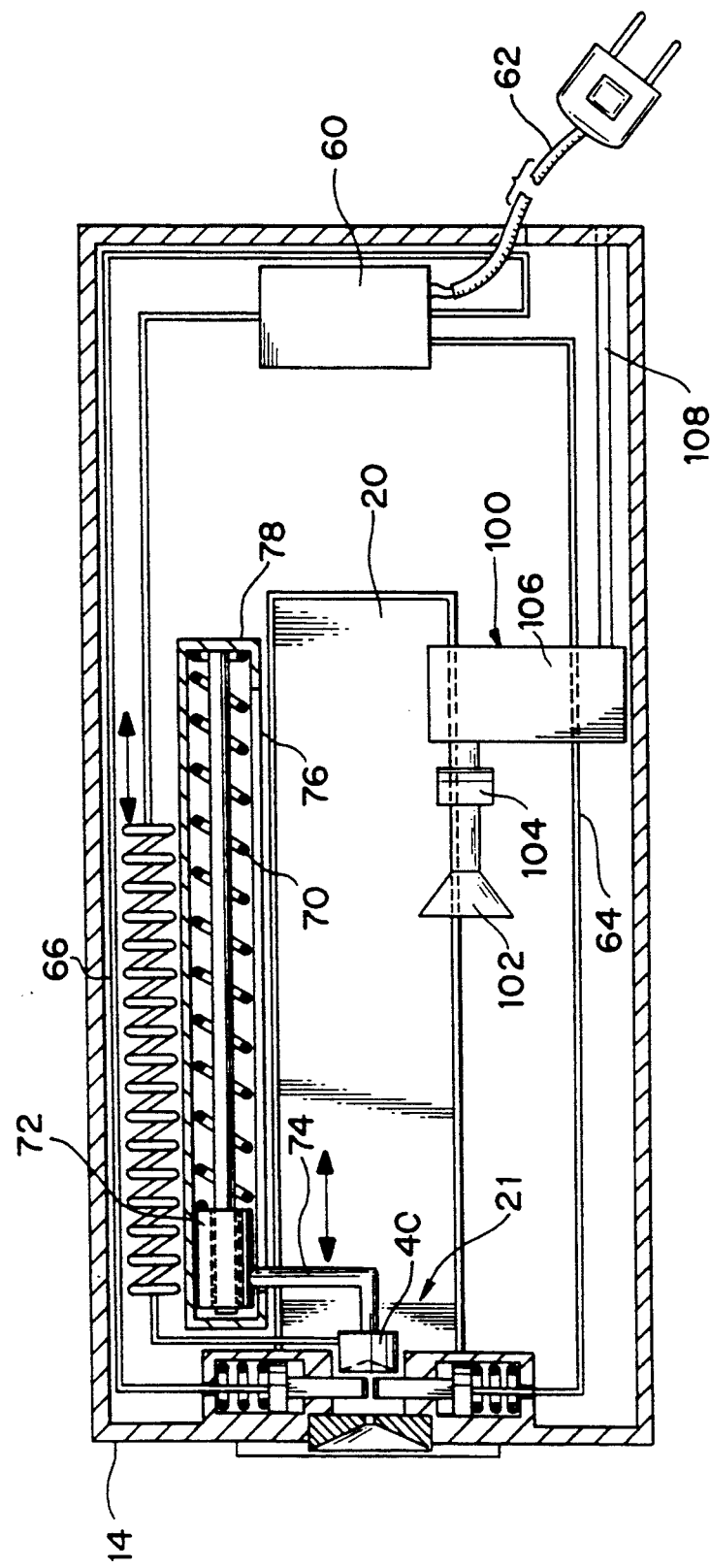
FIG. 4 is a side view of a second embodiment of the present invention wherein a second electrode is mounted for movement with an electrical connection affixed directly to the second electrode.

As illustrated in FIG. 4, a second embodiment of the present invention is set forth wherein the second electrical connector means 40 is mounted on a shaft which is insulated relative to the housing 10. A spring 70 is provided for biasing the second electrical connector means 40 towards the wall 14. An electrical supply line 72 is provided to be operatively connected to the transformer 60 and the second electrical connector means 40. The electrical cable 72 is designed to permit the second electrical connector means 40 to be longitudinally moved within the housing 10. In the embodiment illustrated in FIG. 4, only the second electrical connector means 40 and the first electrical connector means 21 are supplied with electric current. The support structure for the second electrical connector means 40 is insulated and includes a support shaft 74 which is mounted for sliding movement within the housing 76. An abutment 78 is affixed within the housing 76 to engage one end of the spring 70 to provide a mounting surface for the spring 70 so as to permit the spring 70 to bias the support 74 towards the wall 14.

FIG. 5 illustrates another embodiment of the present invention wherein the second electrical connector means 40 is mounted on a pivot arm 80. The pivot arm 80 is pivotally mounted at pivot point 82 relative to the housing 10. A spring 84 may be provided to bias the second electrical connector means 40 towards the wall 14 of the housing 10. Other elements illustrated in FIG. 5 which are similar to the elements discussed hereinabove are referred to with like reference numerals and are not discussed hereinafter.

The present invention may include an exhaust gas filter system 100 which includes a conical exhaust collector 102 operatively connected to a vacuum pump 104 for supplying exhaust gases from the point of the melting of the medical instrument to the electronic precipitator 106. An outlet tube 108 is connected to the electronic precipitator 106 for discharging clean air therefrom. An exhaust gas filter system 100 is not essential for the operation of the apparatus for destroying a medical instrument according to the present invention. However, an exhaust gas filter system 100 may be provided, if desired.

In operation, an individual first actuates the switch 16 to supply electrical current from the supply line 62 to the transformer 60. Thereafter, the needle 50 of the syringe 51 is positioned within the aperture 12 and the tip 50A engages the second electrical connector means 40. The first electrical connector means 24, 34 engages a portion of the needle 50 to form a contact therewith. DC electrical current is supplied from the transformer 60 to the carbon brushes 24, 34 and the second electrical connector means 40. In this way, electrical current is supplied through the needle 50 to melt the needle and destroy any fluids contained therein. The melted needle 50 is no longer a threat to individuals as the syringe 51 is disposed of in an appropriate disposal container. The needle 50 is not capable of pricking an individual to cause any injury to the individual.

During the procedure discussed hereinabove, the plastic or glass container used to form the syringe 51 acts as an insulator to protect the individual as the needle is inserted within the aperture 12. If an individual wishes to dispose of a scalpel or other medical instrument which does not include an insulated handle, it will be necessary to position the scalpel on an insulated handle prior to inserting the scalpel within the aperture. In this way the individual will be insulated as electrical current is supplied through the scalpel to melt the same.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. An apparatus for destroying a medical instrument comprising:

a housing including a wall member with an aperture disposed therein;

first electrical connector means mounted adjacent said wall member of said housing for engaging a first portion of a medical instrument inserted through said aperture in said wall member; and second electrical connector means disposed within said housing for engaging a second portion of a medical instrument inserted through said aperture in said wall member;

said first and second electrical connector means being adapted to be selectively connected to a supply of electric current for destroying a medical instrument by transmitting current from said first electrical connector means to said second electrical connector means and through a medical instrument for melting the same;

said first electrical connector means includes two carbon brushes biased to a position in engagement with each other with respective engaging surfaces being concentric with said aperture in said wall for engaging a medical instrument inserted through said aperture between the two carbon brushes.

2. The apparatus for destroying a medical instrument according to claim 1, wherein said second electrical connector means includes an electrode adapted to engage an end portion of a medical instrument inserted through said aperture, said electrode being mounted for movement within said housing.

3. The apparatus for destroying a medical instrument according to claim 4, wherein said electrode is biased towards the aperture in said wall and mounted for longitudinal movement within said housing for accommodating medical instruments of variable sizes.

4. The apparatus for destroying a medical instrument according to claim 1, and further including an exhaust gas filter including a vacuum pump for collecting exhaust gas and supplying exhaust gas to a filter for removing particles therefrom.

5. An apparatus for destroying a medical instrument comprising:

a housing including a wall member with an aperture disposed therein;

first electrical connector means mounted adjacent said wall member of said housing for engaging a first portion of a medical instrument inserted through said aperture in said wall member; and second electrical connector means disposed within said housing for engaging a second portion of a medical instrument inserted through said aperture in said wall member;

said first and second electrical connector means being adapted to be selectively connected to a supply of electric current for destroying a medical instrument by transmitting current from said first electrical connector means to said second electrical connector means and through a medical instrument for melting the same;

said second electrical connector means includes an electrode adapted to engage an end portion of a medical instrument inserted through said aperture, said electrode being biased towards the aperture in said wall member and mounted in a pivotal relationship within said housing for accommodating medical instruments of variable sizes.

6. The apparatus for destroying a medical instrument according to claim 5, wherein said electrode is biased towards the aperture in said wall and mounted for both pivotal and translational movement within said housing for accommodating medical instruments of variable sizes.

7. The apparatus for destroying a medical instrument according to claim 5, and further including an exhaust gas filter including a vacuum pump for collecting exhaust gas and supplying exhaust gas to a filter for removing particles therefrom.

* * * * *